United States Patent [19]

Fried

[11] Patent Number: 5,401,874

[45] Date of Patent: * Mar. 28, 1995

[54] PREPARATION OF ALKOXYALKANOIC ACIDS

[75] Inventor: Herbert E. Fried, Houston, Tex.

[73] Assignee: Shell Oil Company, Houston, Tex.

[*] Notice: The portion of the term of this patent subsequent to Nov. 10, 2009 has been disclaimed.

[21] Appl. No.: 263,167

[22] Filed: Jun. 21, 1994

Related U.S. Application Data

[63] Continuation of Ser. No. 26,390, Mar. 4, 1993, abandoned.

[51] Int. Cl.$^6$ ............................................. C07C 51/16
[52] U.S. Cl. ....................................... 562/420; 562/540
[58] Field of Search ........................ 562/419, 420, 540

[56] References Cited

U.S. PATENT DOCUMENTS

| | | | |
|---|---|---|---|
| 4,620,033 | 10/1986 | Isshiki et al. | 562/519 |
| 5,136,101 | 8/1992 | Fried | 568/402 |
| 5,136,102 | 8/1992 | Fried | 568/402 |
| 5,136,103 | 8/1992 | Fried | 568/402 |
| 5,155,278 | 10/1992 | Fried | 568/471 |
| 5,155,279 | 10/1992 | Fried | 568/471 |
| 5,155,280 | 10/1992 | Fried | |
| 5,162,579 | 11/1992 | Fried | 562/537 |

(List continued on next page.)

FOREIGN PATENT DOCUMENTS 50-96516  7/1975  Japan .

OTHER PUBLICATIONS

Miyazawa et al., "Oxidation of Benzyl Alcohol with Iron(III) Using Polymers Containing Nitroxyl Radical Structure as a Mediator," J. Polym. Sci., Polym. Chem. Ed., 23 (9), 1985, pp. 2487–2494. (Abstract Only).
Grigor'ev et al., "Participation of Nitroxyl Radical in the Oxidation of Aldehyde and Alcohol Groups in 3-imidazolin-1-oxyls," Izc. Akad. Nauk SSSR, Ser. Khim., (1), 1978, pp. 208–210. (Abstract Only).
Miyazawa et al., "Oxidation of Benzyl Alcohol with Copper(II) Mediated by a Polymeric Oxoaminium Salt," J. Mol. Catal., 49(1), 1988, 131–134. (Abstract Only).
Ganem et al., "Biological Spin Labels as Organic Reagents. Oxidation of Alcohols to Carbonyl Compounds Using Nitroxyls," J. Org. Chem., 40(13), 1975, pp. 1998–2000. (Abstract Only).
Miyazawa et al., "Oxidation of Benzyl Alcohol by Iron-(III) Mediated by Nitroxyl Radical." J. Mol. Catal., 31(2), 1985, pp. 217–220. (Abstract Only).
Annelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52(12), 2559–2562. (1987).
Inokuchi et al., "A Selective and Efficient Method for Alcohol Oxidations Mediated by N-Oxoammonium Salts in Combination with Sodium Bromite," J. Org. Chem., 1990, 55 pp. 462–466.
Organic Synthesis, vol. 69, p. 212 (1990).
Semmelhack et al., "Oxidation of Alcohols to Aldehydes with Oxygen and Cupric Ion, Mediated by Ni- (List continued on next page.)

Primary Examiner—Michael L. Shippen
Attorney, Agent, or Firm—Pamela J. McCollough

[57] ABSTRACT

A process for preparing an alkoxyalkanoic acid by reacting the corresponding alkoxyalkanol with a stable free radical nitroxide in the presence of a $NO_x$-generating compound and, optionally, an oxidant at a temperature in the range of from about 0° C. to about 100° C. and thereafter separating out the alkoxyalkanoic acid.

22 Claims, No Drawings

U.S. PATENT DOCUMENTS

| | | | |
|---|---|---|---|
| 5,166,422 | 11/1992 | Fried | 562/537 |
| 5,166,423 | 11/1992 | Fried | 562/537 |
| 5,175,359 | 12/1992 | Fried | 562/537 |
| 5,175,360 | 12/1992 | Fried | 562/538 |
| 5,179,218 | 1/1993 | Fried | 554/134 |
| 5,250,727 | 10/1993 | Fried | 562/540 |

OTHER PUBLICATIONS trosonium Ion," J. Am. Chem. Soc., 1984, 106, 3374–3376.

Yamaguchi et al., "Application of Redox System Based on Nitroxides to Organic Synthesis," Pure & Applied Chemistry, vol., 62(2), 1990, 217–222.

E. R. Kagan et al., "Chemistry of Hindered Amines from the Piperidine Series", Synthesis, pp. 895–916. (1984).

R. M. Dupeyre et al., "Nitroxides. XIX. Norpseudopelletierine-N-oxyl, a New, Stable, Unhindered Free Radical," pp. 3180–3818. (1966).

E. R. Rozantsev et al., "Synthesis and Reaction of Stable Nitroxyl Radicals I. Synthesis" Synthesis, Apr. 1971, pp. 190–202.

E. R. Rozantsev et al., "Synthesis and Reaction of Stable Nitroxyl Radicals II. Reactions," Synthesis, Apr. 1971, pp. 401–414.

PREPARATION OF ALKOXYALKANOIC ACIDS

This is a continuation of application Ser. No. 026,390, filed Mar. 4, 1993, now abandoned.

FIELD OF THE INVENTION

This invention relates to a process for the preparation of alkoxyalkanoic acids by the oxidation of the corresponding alkoxyalkanols in the presence of a stable free radical nitroxide and a $NO_x$-generating compound and, optionally, an oxidant.

BACKGROUND OF THE INVENTION

Alkoxyalkanoic acids are useful as anionic surfactants or emulsifying agents. These acids, being composed of only the elements C, H and O, do not pose the environmental problems that other detergents containing heteroatoms such as N, S, and P pose. The alkoxyalkanoic acids can be prepared in a two-step process of first reacting an alkanol with an alkoxylate and a suitable alkoxylation catalyst and thereafter converting the resultant alkoxyalkanol to the alkoxyalkanoic acid.

It is also known to convert alkoxyalkanols such as methyl carbitol to the corresponding carboxylic acids by oxidizing them with nitric acid. However, relatively large amounts of nitric acid are required and not all of the nitric acid can be separated by distillation. In addition, cleavage of the ether linkages occurs to a large degree during this process.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2559–2562; *Pure and Applied Chemistry*, vol. 62(2), 1990, pp. 217–222; *Journal of Organic Chemistry*, vol. 55, 1990, pp. 462–466. The primary products produced in these processes are aldehydes and the stoichiometrically consumed oxidant is hypochlorite.

It is generally more difficult to oxidize alkoxyalkanols than alkanols as it is difficult to oxidize alkoxyalkanols without splitting the molecular chain at the ether linkage and thereby produce a large proportion of undesired by-product. It would therefore be advantageous to produce alkoxyalkanoic acids in high yields and with high selectivities without producing large amounts of other products such as aldehydes, esters, and alkanoic acids.

It has been found that alkoxyalkanoic acids having high selectivities can be produced without forming highly corrosive, difficult to separate, side-products by using catalytic amounts of a stable free radical nitroxide, a $NO_x$-generating compound and, optionally, an oxidant.

SUMMARY OF THE INVENTION

This invention relates to a process for the preparation of an alkoxyalkanoic acid of the formula $$RO(CH_2CHR'O)_nCH_2CO_2H$$

wherein R is or an alkyl group of from 1 to about 22 carbon atoms, R' is hydrogen, alkyl, aryl or mixtures thereof (on the individual molecule) and n is an integer of from 1 to about 12 which comprises reacting the corresponding alkoxyalkanol with a stable free radical nitroxide having the formula:

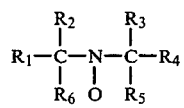

wherein (1) (a) each of $R_1$, $R_2$, $R_3$ and $R_4$ is an alkyl, aryl or substituted alkyl group having 1 to about 15 carbon atoms, and (b) $R_5$ and $R_6$ (i) together form a five-membered ring containing at least 3 carbon atoms and up to 2 heteroatoms of O or N, or (ii) together form part of a ring that contains at least 6 carbon atoms and up to two heteroatoms of O or N, or (2) the

moiety and the

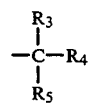

moiety together form a bicyclic ring with the proviso that the group directly adjacent to the N—O moiety is a bridgehead C—H, or a fully alkylated carbon, in the presence of a $NO_x$-generating compound and, optionally, an oxidant at a temperature in the range of from about 0° C. to about 100° C. and thereafter separating out the alkoxyalkanoic acid.

DESCRIPTION OF THE PREFERRED EMBODIMENTS

The present process converts alkoxyalkanols of the formula $$RO(CH_2CHR'O)_nCH_2CH_2OH \qquad (I)$$

wherein R is an alkyl group, preferably 1 to about 22; more preferably about 11 to about 18 carbon atoms, R' is hydrogen, alkyl, aryl or mixtures thereof (on the individual molecule) and n represents the average number of oxyalkylene groups and is an integer of from 1 to about 12, preferably from about 2 to about 9, to the corresponding alkoxyalkanoic acids of the formula:

$$RO(CH_2CHR'O)_nCH_2CO_2H \qquad (II)$$

by contacting the alkoxyalkanol with a stable free radical nitroxide in the presence of a $NO_x$-generating compound and, optionally, an oxidant at a temperature in the range of from about 0° C. to about 100° C. and thereafter separating out the alkoxyalkanoic acid. The alkyl group, R, in the above formula I can be substituted with any substituent which does not interfere with the oxidation of the hydroxy group. Such substituents include —OR", —CH$_3$, —COOH, CONH$_2$ and COOR" wherein R" is an alkyl or aryl group.

The process of the instant invention is particularly suited to ethoxylated, or propoxylated alcohols with alkyl chains (R) of about 8 to about 20, preferably of about 11 to about 18 carbon atoms. The R' groups on an individual molecule can be hydrogen, alkyl, aryl or mixtures thereof. For example, straight ethoxylated, straight propoxylated and mixed ethoxylated-propoxylated detergent alcohols are available. The number of such alkoxylate groups, (CH$_2$CHR'O), typically ranges from about 1 to about 12. Commercially, detergent range ethoxylated alcohols are available with an average of 3, 7, 9 and 12 ethoxylate units per molecule. Others can be readily prepared. In a preferred embodiment, the starting alkoxyalkanol is an ethoxylated alcohol which has had the unreacted alcohols and lower ethoxylates topped off in order to give an ethoxylated alcohol having about 3 to about 4 ethylene oxide units per molecule.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in-situ.

The stable free radical nitroxides, as used in the present process, are precursors to catalysts, i.e., oxoammonium salts, active for the oxidation of alkoxyalkanols to the corresponding acids. These catalysts are generated in situ by the oxidation of a stable free radical nitroxide to an oxoammonium salt. The stable free radical nitroxide can be obtained by the oxidation of secondary amines or hydroxylamines.

The stable free radical nitroxides which are suitable for use in the instant invention have the formula:

$$\begin{array}{c} R_2 \quad R_3 \\ | \quad | \\ R_1-C-N-C-R_4 \\ | \quad | \quad | \\ R_6 \quad O \quad R_5 \end{array} \quad (III)$$

wherein each of R$_1$, R$_2$, R$_3$ and R$_4$ is an alkyl, aryl or substituted alkyl group and no hydrogen is bound to the remaining valences of the carbon atoms bound to the nitrogen. As used herein the term "alkyl" is meant to include cycloalkyl. The alkyl (or heteroatom substituted) groups R$_1$–R$_4$ may be the same or different, and preferably contain 1 to 15 carbon atoms. Preferable, R$_1$–R$_4$ are methyl, ethyl, or propyl groups. In addition to hydrogen, the heteroatom substituents may include, halogen, oxygen, nitrogen and the like, as long as such substituents do not interfere with the oxidation reaction.

The remaining valences (R$_5$ and R$_6$) in formula III above together may form a five-membered ring containing at least 3 carbon atoms and up to 2 heteroatoms of O or N, or form part of a ring that contains at least 6 carbon atoms and up to two heteroatoms of O or N. R$_5$ and R$_6$ can, for example, form a five-membered ring containing 3 carbon atoms and up to two heteroatoms, such as O or N, a five-membered ring containing 4 carbon atoms, a seven-membered ring containing 6 carbon atoms, or an eight-membered ring containing 7 carbon atoms, etc. For purposes of this invention, it is preferred that R$_5$ and R$_6$ together form a five-membered ring, a seven-membered ring, or an eight-membered ring, although larger rings would also be suitable. Examples of suitable compounds having the structure above and in which R$_5$ and R$_6$ form part of the ring are 2,2,5,5-tetramethylpyrrolidin-1-oxyl, 2,2,4,4-tetramethyl-3-oxazolidin-1-oxyl, 1-aza-2,2,7,7-tetramethylcycloheptan-1-oxyl and mixtures thereof. It is understood that these compounds may contain substituents which do not interfere with the reaction. The

and the

moieties in formula III above can also form a bicyclic ring wherein the group adjacent to the N—O moiety is either a bridgehead C—H or a quarternary carbon. As used herein, the term "bridgehead C—H" refers to a tertiary carbon which is common to both rings of the bicyclic ring system. As used herein, "a quarternary carbon" refers to a fully substituted carbon atom having alkyl, aryl or substituted alkyl groups having 1 to about 15 carbon atoms as substituents. Examples of suitable compounds having the structure above in which the $$\begin{array}{c} R_2 \\ | \\ R_1-C- \\ | \\ R_6 \end{array}$$

and the $$\begin{array}{c} R_3 \\ | \\ -C-R_4 \\ | \\ R_5 \end{array}$$

moieties form a bicyclic ring are 2-azabicyclo[2.2.1]heptan-2-oxyl, 2-azabicyclo[2.2.2]-3,3-dimethyloctan-2-oxyl, 3-azabicyclo[3.2.2]-2,2,4,4-tetramethylnonan-3-oxyl and the like. These compounds may be substituted with any substituents which do not interfere with the reaction. In a preferred embodiment, the stable free radical nitroxide is a 2,2,5,5-tetramethylpyrrolidin-1-oxyl having the formula:

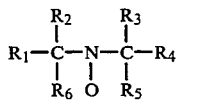

(IV)

wherein each of R$_7$ and R$_8$ is hydrogen, an alkyl, or any substituent which does not interfere with the oxidation reaction such as, for example, CONH$_2$, COOH and the like. A particularly preferred 2,2,5,5-tetramethylpyrrolidin-1-oxyl for use in the present invention is 3-carbamoyl-2,2,5,5-tetramethylpyrrolidin-1-oxyl, which has the formula:

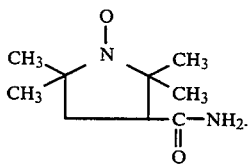

(V)

The NO$_x$-generating compound in the present process is typically selected from the group consisting of an alkali metal nitrosodisulfonate, nitric acid and mixtures thereof, with nitric acid being preferred. However, any compound which serves to generate NO$_x$ during the course of the reaction and which does not interfere with the reaction would be suitable. While not wishing to be bound by any particular theory, it is believed that nitrogen oxides (NO$_x$) are generated in the reaction and are required to generate the active catalytic species.

The alkali metal nitrosodisulfonate suitable for use as a NO$_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added. Generally, the amount of alkali metal nitrosodisulfonate used is in the range of from about 5 mole percent to about 1000 mole percent, basis the moles of starting alkoxyalkanol.

As used herein, the term "nitric acid" refers to nitric acid, fuming nitric acid or nitrous acid generated by contacting alkali metal nitrite with mineral acid. Nitric acid can also be generated by contacting alkali metal nitrate with mineral acid. The nitric acid suitable for use in the present invention typically has a concentration in the range of from about 50 percent to about 100 percent, preferably about 70 percent. Generally, an amount of nitric acid in the range of from about 5 mole percent to about 1000 mole percent, basis the moles of starting alkoxyalkanol is utilized. The nitric acid is typically added to the reaction mixture after all of the other reactants have been added.

The process of the present invention may be carried out in the presence or absence of an oxidant. In a preferred embodiment, the process is carried out in the presence of an oxidant. The oxidants suitable for use in the instant invention are those compounds which are capable, in the presence of nitric acid, of oxidizing the stable free radical nitroxide to the oxoammonium salt. Suitable oxidants include oxygen-containing gases such as pure oxygen and oxygen in air. Whereas pure oxygen is preferred to accomplish the desired conversion, the oxygen can also be diluted with an inert gas such as nitrogen, helium, argon, or other similar gas. While air can be used as the oxidant, the reaction rate is slower. For purposes of increasing the reaction rate, higher O$_2$ pressures such as, for example, 1000 psig can be utilized. In a preferred embodiment, pure oxygen is used as the oxidant and it is bubbled into the reaction solution.

The reaction in the instant invention can be carried out in the presence or absence of a solvent. When the reaction is carried out in the presence of a solvent, the solvent is generally a solvent in which the alkoxyalkanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, tertiary alcohols such as tertiary butyl alcohol, dichloromethane, chlorobenzene, chloroform, carbon tetrachloride, dichloroethylene, dimethoxyethane and mixtures thereof. In a preferred embodiment, the solvent is selected from the group consisting of acetonitrile, dichloromethane and mixtures thereof. The ratio of solvent to starting alkoxyalkanol utilized in the process is typically in the range of from about 20:1 to about 0.5:1 and preferably in the range of from about 5:1 to about 1:1.

The amounts and concentrations of the reactants utilized in the process of the instant invention can vary within wide ranges. The amount of stable free radical nitroxide is typically in the range of from about 1 mole percent to about 500 mole percent, preferably from about 5 mole percent to about 20 mole percent, basis the number of moles starting alkoxyalkanol. Generally, when from about 5 mole percent to about 20 mole percent of free radical nitroxide is utilized, it is desirable to use an oxidant. Generally, the amount of NO$_x$-generating compound used is in the range of from about 5 mole percent to about 1000 mole percent, basis the number of moles of alkoxyalkanol.

The process of the present invention is typically conducted under mild conditions, with good results being obtained using a temperature in the range of from about 0° C. to about 100° C., preferably about 20° C. to about 70° C., and most preferably, about 40° C. to about 60° C.. When an alkali metal nitrodisulfonate is utilized as the NO$_x$-generating compound, a temperature of from about 0° C. to about 60° C. is preferred, and a temperature in the range of from about 30° C. to about 40° C. is particularly preferred. Reaction pressures are not critical although higher pressures may result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.016 moles of alkoxyalkanol, and 0.016 moles percent by weight of the nitroxide, may be added to the reaction vessel, followed by the addition of 0.029 moles of 70 percent nitric acid. The reaction vessel may then be left open to the atmosphere. Following the reaction, the product may be separated from the reaction mixture using conventional procedures such as extraction using a suitable extraction solvent such as, for example, dichloromethane; evaporation wherein the solvent is stripped from the reaction mixture by using heat or vacuum. The reaction product can be purified by a number of conventional means such as high temperature water washing or catalytic hydrogenation.

Depending upon process conditions and the nitroxide used, the selectivity to alkoxyalkanoic acids obtained by this invention can be greater than about 65%. The products produced by the instant process can be used as emulsifying agents or in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a NEODOL® Ethoxylate 23-3T alcohol which was prepared by ethoxylating a mixture of $C_{12}$ and $C_{13}$ substantially straight chain alcohols ($C_{12}$:$C_{13}$ 40:60) to an ethoxylated alcohol having about 3 ethylene oxide units per molecule and then topping off the unreacted alcohols and lower ethoxylates so that the final product contains less than about 5 percent unreacted alcohol.

Example 1

6.3 Grams of the starting alkoxyalkanol, 3 grams of 3-carbamoylproxyl, 25 milliliters of acetonitrile and 2.6 grams of 70 percent nitric acid were charged to a 100 milliliter round bottomed flask. This mixture was left open to the atmosphere. The reaction temperature was held at 35° C. over a 6-hour period. The results are presented in Table I.

Example 2

6.3 Grams of the starting alkoxyalkanol, 1.5 grams of 3-carbamoyl-proxyl, 25 milliliters of dichloromethane and 1 gram of 70 percent nitric acid were charged to a 100 milliliter round bottomed flask. $O_2$ was then sparged through the reaction vessel. The reaction was held at 35° C. over a 3-hour period. The results are presented in Table I.

Example 3

12 Grams of the starting alkoxyalkanol, 1.2 grams of 3-carbamoyl-proxyl, 25 milliliters of dichloromethane, and 1 gram of 70 percent nitric acid were charged to a 100 milliliter glass vessel. $O_2$ was then sparged through the reaction vessel. The reaction temperature was held at 35° C. over a 6-hour period. The results are presented in Table I.

Comparative Example A

Comparative Example A was carried out in a manner similar to Example 2 except that no nitroxide was used. The results are presented in Table I.

Comparative Example B

Comparative Example B was carried out in a manner similar to Example 2 except that no nitric acid was used. The results are presented in Table I.

As can be seen in Table I, both nitroxide and nitric acid are necessary for the oxidation of the alkoxyalkanol to proceed.

TABLE I

| Oxidation of Alkoxyalkanols to Alkoxyalkanoic Acids | | | | |
|---|---|---|---|---|
| | % Conversion | % Selectivity to Acids | % Selectivity to Esters | % Selectivity to Aldehydes (hemi-acetals) |
| Example 1 | 41 | 85 | 5 | 10 |
| Example 2 | 10 | 73 | 9 | 18 |
| Example 3 | 15 | 67 | none detected | 33 |
| Comparative Example A | 0 | 0 | 0 | 0 |
| Comparative Example B | 3 | 0 | none detected | 66 |

What is claimed is:

1. A process for the preparation of an alkoxyalkanoic acid of the formula $RO(CH_2CHR'O)_nCH_2CO_2H$ wherein R is an alkyl group of from 1 to about 22 carbon atoms, R' is hydrogen or methyl or mixtures thereof (on the individual molecule) and n is an integer of from 1 to about 12, which comprises reacting the corresponding alkoxyalkanol with a stable free radical nitroxide selected from the group consisting of 2,2,5,5-tetramethylpyrrolidin-1-oxyl, 2,2,4,4-tetramethyl-3-oxazolidin-1-oxyl, 1-aza-2,2,7,7-tetramethylcycloheptan-1-oxyl, and mixtures thereof in the presence of a $NO_x$-generating compound selected from the group consisting of an alkali metal nitrosodisulfonate, nitric acid and mixtures thereof, at a temperature in the range of from about 0° C. to about 100° C. and thereafter separating out the alkoxyalkanoic acid.

2. The process of claim 1 wherein the stable free radical nitroxide is 3-carbamoyl-2,2,5,5-tetramethylpyrrolidin-1-oxyl and has the formula:

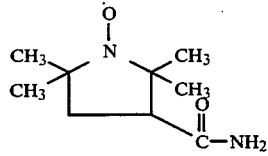

3. The process of claim 1 therein the stable free radical nitroxide is a bicyclic ring selected from the group consisting of 2-azabicyclo[2.2.1]heptan-2-oxyl, 2-azabicyclo[2.2.2]-3,3-dimethyloctan-2-oxyl, 3,-azabicyclo[3.2.2]-2,2,4,4-tetramethylnonan-3-oxyl and mixtures thereof.

4. The process of claim 1 wherein said $NO_x$-generating compound is nitric acid.

5. The process of claim 4 wherein said nitric acid is selected from the group consisting of fuming nitric acid, nitrous acid generated by contacting an alkali metal nitrite with mineral acid, nitric acid generated by contacting an alkali metal nitrate with mineral acid, and mixtures thereof.

6. The process of claim 4 wherein said nitric acid has a concentration in the range of from about 50 percent to about 100 percent.

7. The process of claim 4 wherein the amount of nitric acid is in the range of from about 5 mole percent to about 1000 mole percent, basis the number of moles alkoxyalkanol.

8. The process of claim 1 wherein said $NO_x$-generating compound is an alkali metal nitrosodisulfonate.

9. The process of claim 8 wherein the amount of alkali metal nitrosodisulfonate is in the range of from about 5 mole percent to about 1000 mole percent, basis the number of moles of alkoxyalkanol.

10. The process of claim 8 wherein said alkali metal nitrosodisulfonate is potassium nitrosodisulfonate.

11. The process of claim 1 wherein said process is carried out in the presence of a solvent.

12. The process of claim 11 wherein said solvent is selected from the group consisting of acetonitrile, tertiary alcohols such as tertiary butyl alcohol, dichloromethane, chlorobenzene, chloroform, carbon tetrachloride, dichloroethylene, dimethoxyethane and mixtures thereof.

13. The process of claim 12 wherein said solvent is selected from the group consisting of acetonitrile, dichloromethane and mixtures thereof.

14. The process of claim 1 wherein said alkoxyalkanol is contacted with said stable free radical nitroxide, followed by the addition thereto of said $NO_x$-generating compound and said oxidant.

15. The process of claim 14 wherein the amount of stable free radical nitroxide is in the range of from about 1 mole percent to about 500 mole percent, basis the number of moles of alkoxyalkanol.

16. The process of claim 15 wherein the amount of stable free radical nitroxide is in the range of from about 5 mole percent to about 20 mole percent, basis the number of moles of alkoxyalkanol.

17. The process of claim 14 wherein the amount of $NO_x$-generating compound is in the range of from about 5 mole percent to about 1000 mole percent, basis the number of moles of alkoxyalkanol.

18. The process of claim 1 wherein said process is carried out in the presence of an oxidant.

19. The process of claim 18 wherein said oxidant is an oxygen-containing gas.

20. The process of claim 19 wherein said oxygen-containing gas is selected from the group consisting of pure oxygen and air.

21. The process of claim 20 wherein said oxygen-containing gas is pure oxygen.

22. The process of claim 1 wherein said process is carried out at a temperature in the range of from about 20° C. to about 70° C. and at atmospheric pressure.

* * * * *